United States Patent [19]

Brunnmueller et al.

[11] Patent Number: 4,745,207

[45] Date of Patent: May 17, 1988

[54] PREPARATION OF THE REACTION PRODUCTS OF HYDROGEN CYANIDE

[75] Inventors: Fritz Brunnmueller, Limburgerhof; Karlheinz Stecher, Ludwigshafen; Michael Kroener; Rolf Schneider, both of Mannheim, all of Fed. Rep. of Germany

[73] Assignee: BASF Aktiengesellschaft, Ludwigshafen, Fed. Rep. of Germany

[21] Appl. No.: 802,058

[22] Filed: Nov. 25, 1985

[30] Foreign Application Priority Data

Nov. 29, 1984 [DE] Fed. Rep. of Germany ....... 3443462

[51] Int. Cl.$^4$ ................................................ C01C 3/04
[52] U.S. Cl. ................................... 558/351; 423/372; 423/373; 423/379; 558/346; 558/453; 564/511
[58] Field of Search ......................... 423/372, 373, 379; 558/346, 351, 453; 564/511

[56] References Cited

U.S. PATENT DOCUMENTS

| | | | |
|---|---|---|---|
| 1,846,221 | 2/1932 | Michael et al. | 423/373 |
| 2,429,262 | 10/1947 | Fallows et al. | 423/373 |
| 2,529,546 | 11/1950 | Fallows et al. | 423/373 |
| 3,702,887 | 11/1972 | Sennewald et al. | 423/373 |
| 4,230,772 | 10/1980 | Swift et al. | 428/442 |

FOREIGN PATENT DOCUMENTS 1014094 12/1957 Fed. Rep. of Germany .
1211612 3/1966 Fed. Rep. of Germany .

OTHER PUBLICATIONS

Kirk-Othmer, *Encyclopedia of Chemical Technology*, Third Edition, vol. 7, John Wiley & Sons (1981), pp. 307–310.

*Primary Examiner*—John Doll
*Assistant Examiner*—Wayne A. Langel
*Attorney, Agent, or Firm*—Oblon, Fisher, Spivak, McClelland & Maier

[57] ABSTRACT

Reaction products of hydrogen cyanide are prepared by a process in which hydrogen cyanide prepared in a conventional manner by pyrolysis at from 250° to 650° C. over a solid under from 5 to 200 mbar is cooled to a temperature of from 200° to −10° C. together with the other pyrolysis products, the hydrogen cyanide is then fed to a chemisorption reaction with a base or with a carbonyl compound, and the reaction products of hydrogen cyanide which are formed therein are removed from the system and brought to atmospheric pressure. In this process, the handling of large amounts of hydrogen cyanide is avoided.

6 Claims, No Drawings

PREPARATION OF THE REACTION PRODUCTS OF HYDROGEN CYANIDE

German Pat. No. 1,211,612 discloses the preparation of hydrogen cyanide by the formamide vacuum process, in which formamide is vaporized under reduced pressure and cleaved catalytically to give hydrogen cyanide and water, heat being supplied. In an undesirable side reaction, formamide is converted to small amounts of ammonia and carbon monoxide under the pyrolysis conditions. However, since ammonia catalyzes the polymerization of hydrogen cyanide, it is impossible, in the conventional process, to dispsense with the step in which ammonia is removed from the cleavage gas by washing with a non-volatile acid. The washed cleavage gas is then compressed to atmospheric-pressure, substantially liquefied by cooling and, if required, fed to a distillation plant for working up to pure hydrogen cyanide, which can then be converted to reaction products, such as sodium cyanide or acetone cyanohydrin, which are relatively safe to handle.

It is known that pumps possessing mechanically moved parts, eg. single-stage or multi-stage reciprocating compressors or centrifugal pumps, can be used for generating the reduced pressure required for the pyrolysis. However, these units have the disadvantage that the hydrocyanic acid readily polymerizes therein to form dark solid products which block the plant and frequently interrupt operation. Blockages due to hydrogen cyanide polymers are observed in particular in the cylinders and valve casings of the compressors and in the pipelines and parts of the apparatus on the pressure side of the compressors. Accordingly to German Pat. No. 1,211,612, the formation of polymers can be substantially avoided if the temperature of the hydrogen cyanide-containing cleavage gas at the exit of the pressure side of the plant compressor is set at 55°–80° C., preferably 60°–70° C.

In another conventional procedure, polymerization of the hydrogen cyanide does not take place during the preparation of the hydrogen cyanide if, instead of the reciprocating compressors, a steam jet ejectors are used for generating the reduced pressure. However, this has other disadvantages, so that steam jet ejectors, too, have proven unsatisfactory in industry.

In the conventional processes for the preparation of hydrogen cyanide, other disadvantages have to be accepted. For example, condensates containing lubricating oil have to be removed regularly at the lowest point of the plant, the pressure side of the plants has to be flushed regularly, or stabilizers which prevent or suppress polymerization of the hydrogen cyanide have to be used.

However, a fundamental problem in the preparation of hydrogen cyanide concerns the compression of very large amounts of cleavage gas, very expensive compressors requiring frequent repair being required for this purpose. For example, around 7,750 m$^3$/hour of gas have to be washed with sulfuric acid to remove ammonia and then compressed, these tests being carried out under 80 mbar and with a feed of 900 kg/hour of formamide. Carrier gas and the cleavage gases, such as carbon monoxide, carbon dioxide and hydrogen, which originate from side reactions are also present. The water-containing hydrocyanic acid compressed to atmospheric pressure in this manner must be condensed and distilled and can only be further processed to aqueous sodium cyanide solution, after removal of carbon dioxide, with sodium hydroxide solution.

It is an object of the present invention to provide a technically simpler process for the preparation of reaction products of hydrogen cyanide in conjunction with the preparation of hydrogen cyanide by pyrolysis. Particular value is laid on a high level of operational safety in the process.

We have found that this object is achieved, in accordance with the invention, by a process for the preparation of reaction products of hydrogen cyanide by reacting the latter with a base or a carbonyl compound, if hydrogen cyanide prepared by pyrolysis at from 250° to 650° C. over a solid as a catalyst and from 5 to 200 mbar is cooled, together with the other pyrolysis product, to a temperature of from 200° to −10° C., the hydrogen cyanide is then fed to a chemisorption reaction with the base or carbonyl compound, and the resulting condensate of hydrogen cyanide is removed from the system and brought to atmospheric pressure.

The hydrogen cyanide is prepared under reduced pressure by pyrolysis of a compound which eliminates hydrogen cyanide at from 250° to 650° C. Preferably formamide is used as the compound which eliminates hydrogen cyanide, although it is also possible to use a large number of other compounds. Of particular interest in this context are N-acyl derivatives of 1-amino-1-cyanoethane or its substitution products, with which it is possible to convert these compounds not only to hydrogen cyanide but also to other substances which, for example, are used for monomers, ie. N-vinyl-N-acylamides and the substituted products. The N-acyl derivatives of 1-amino-1-cyanoethane are, for example, of the formula

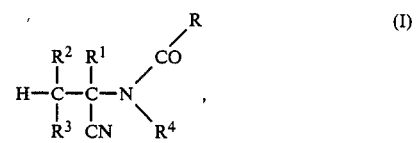

where
R, R$^1$, R$^2$ and R$^3$ are each H or C$_1$–C$_6$-alkyl,
R$_1$ and R$^2$ or R$^2$ and R$^3$ together form a carbocyclic ring of 5 or 6 carbon atoms and
R$^4$ is H or C$_1$–C$_6$-alkyl.

For example, the compound of the formula

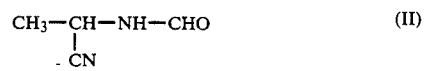

undergoes a smooth reaction to give hydrogen cyanide and N-vinylformamide (CH$_2$=CH—NH—CHO), while the compound of the formula

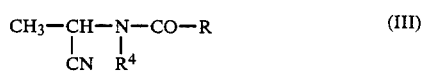

where
R is H and R$^4$ is CH$_3$, gives N-vinylmethylformamide and HCN and the compound of the formula III where R and R$^4$ are each CH$_3$ gives N-vinyl-N-methylacetamide and HCN.

Here, the evolution of hydrogen cyanide can be coupled to the preparation of industrially useful monomers.

The compounds of the formula I and the pyrolysis of these is disclosed in German Pat. Nos. 1,224,304 and 1,228,246.

The compounds which eliminate hydrogen cyanide are pyrolyzed over solids, suitable solids for this purpose being those stated in, for example, German Pat. No. 1,224,304, as well as alkali metal and alkaline earth metal carbonates, such as sodium carbonate, potassium carbonate, magnesium carbonate, strontium carbonate, barium carbonate, marble, dolomite, chalk and magnetite. Catalysts which have proven particularly advantageous are those which contain alkali metal or alkaline earth metal carbonates on α-alumina as a carrier. Calcium carbonate, dolomite or mixtures of calcium carbonate and magnesium carbonate on α-alumina are preferably used. Catalysts of this type are prepared by impregnating α-alumina with water-soluble salts, eg. calcium acetate, and converting the salts to the corresponding carbonates or oxides by means of a thermal treatment.

Pyrolysis is carried out at from 250° to 650° C., preferably from 300° to 550° C., under from 5 to 200, preferably from 10 to 150 mbar. The pyrolysis products, which, depending on the conditions in the pyrolysis zone, may contain larger or smaller amounts of unconverted starting material, are cooled to a temperature of from 200° to $-10°$ C., preferably from 60° to $-10°$ C., under the pressure conditions prevailing in the pyrolysis zone. In this stage of the process, all products having a boiling point higher than that of hydrogen cyanide are condensed. The amount of hydrogen cyanide removed from the pyrolysis gas depends only on the solubility of the hydrogen cyanide in the condensed products. If the compounds of the formula (I) are used for obtaining hydrogen cyanide, the N-vinylamides are obtained in the stage in which the pyrolysis gas is cooled to a temperature of from 200° to $-10°$ C. In the process according to the invention, formamide is preferably pyrolyzed.

The uncondensed hydrogen cyanide is then subjected to chemisorption, likewise under reduced pressure under which the pyrolysis too takes place, the only difference compared with the pyrolysis being a pressure loss due to the procedure. The pressure in the chemisorption zone of the process is from 5 to 200, preferably from 5 to 45, mbar when the hydrogen cyanide is produced from the compounds of the formula I, and from 20 to 60 mbar when the hydrogen cyanide is prepared from formamide. For example, sodium hydroxide solution or potassium hydroxide solution is used for chemisorption of the hydrogen cyanide and hence for the preparation of reaction products of this. In these cases, the sodium and potassium salts of hydrocyanic acid are obtained. Other absorbents for hydrogen cyanide are carbonyl compounds, examples of suitable ones being aldehydes of 1 to 8 carbon atoms, such as formaldehyde, acetaldehyde, propionaldehyde, n-butyraldehyde, isobutyraldehyde and 2-ethylhexanal. Other suitable carbonyl compounds are ketones such as acetone and methyl ethyl ketone. The chemisorption of the hydrogen cyanide with carbonyl compounds is carried out at a pH of 7 or above, and preferably at an alkaline pH, since the reaction takes place very rapidly under these conditions. If formamide is employed in the pyrolysis, the cleavage gas contains ammonia, which passes through the condensers together with the hydrogen cyanide and ensures a sufficiently high pH in the chemisorption stage. However, inorganic or organic bases may be introduced into the chemisorption stage in addition, or if the cleavage gas contains only a small amount of ammonia. The reaction between the hydrogen cyanide and the carbonyl compound is usually preferably catalyzed using a tertiary amine, eg. triethylamine. In the chemisorption of the hydrogen cyanide with carbonyl compounds, amines which carry one or more hydrogen atoms on the nitrogen may additionally be used. In these cases, aminonitriles are obtained as reaction products of hydrogen cyanide, in a Strecker synthesis. Amines which are preferably used here are compounds of the formula

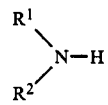

where $R^1$ and $R^2$ are each $C_1$–$C_8$-alkyl or H. Hydrogen cyanide, the amine and the carbonyl compound are preferably used in the chemisorption in a molar ratio of 1:1:1.

The addition reaction of hydrogen cyanide with aldehydes of 1 to 4 carbon atoms or with secondary amines under the pressure conditions prevailing during the pyrolysis takes place at a rate such that a single-stage chemisorption is sufficient. However, the chemisorption may be carried out in several steps, for example in two or more columns connected in series. The temperature during the chemisorption is from $-20°$ to $+30°$ C., preferably from $-5°$ to $+15°$ C. If the reaction rate during the chemisorption with carbonyl compounds decreases, it is usual to employ a multistage procedure. The chemisorption may be carried out in the presence or absence of a solvent. Examples of suitable solvents are water, formamide and amines. If salts of hydrogen cyanide are being prepared, a solvent cannot be dispensed with in the chemisorption, because the salts formed during the chemisorption must be kept in solution.

It is surprising that, under the pressure conditions prevailing during pyrolysis, ie. from 5 to 200 mbar, two substances having such low boiling points, eg. hydrogen cyanide (bp. 27° C. under atmospheric pressure) and acetaldehyde (bp. 21° C. under atmospheric pressure), can be converted virtually quantitatively to lactonitrile at $+10°$ C. Plus, it is now possible to dispense with the production of fairly large amounts of liquid hydrogen cyanide (as much as 540 kg/hour of HCN for a production of 20 kmol/hour) as a starting material for the preparation of reaction products of hydrogen cyanide. The amounts of of hydrogen cyanide which are formed during the pyrolysis are processed in the chemisorption stage directly to the much less hazardous reaction products of hydrogen cyanide. The hydrogen cyanide content of these reaction products is as a rule less than 0.1% by weight. Preparation of reaction products of hydrogen cyanide by this method ensures a high level of safety even when faults occur during operation; for example, in the event of the particularly feared leakage in the pressure apparatus, the formation of hydrogen cyanide stops immediately and automatically, and hence any further evolution of hydrogen cyanide can be stopped. This makes it possible to set up much less problematic, small units for the production of secondary products of hydrogen cyanide, for example for the preparation of acetone cyanohydrin or amino acids, at virtually any sites. Another technical advantage of the novel process over the prior art is that a $CO_2$ wash is completely superfluous in the synthesis of cyanohydrin or of aminonitrile. Furthermore, an ammonia wash is no longer necessary when formamide is used to form hydrogen cyanide.

Apart from the pressure lost, pyrolysis, condensation and chemisorption take place under the same pressure conditions, ie. from 5 to 200 mbar. The pyrolysis and chemisorption are always carried out by a continuous procedure, in which the hydrogen cyanide formed continuously during the pyrolysis is fed to the chemisorption stage at the rate at which it is formed, and condensation of the hydrogen cyanide is dispensed with. The chemisorption may be carried out in a variety of ways. For example, the hydrogen cyanide can be passed into an excess of the absorbent, eg. acetone, or the chemisorption can be carried out by a circulatory procedure in which the absorbent, in the presence or absence of a solvent, such as formamide, is circulated through a column connected inbetween, fresh absorbent and, if required, fresh solvent and other substances are metered into the circulated mixtures, in each case upstream of the entrance to the column, and, down-stream of the chemisorption, the solution is collected in a container, which is likewise under reduced pressure, and is discharged from this container at the rate at which material is fed in upstream of the column. As a result of this procedure, the system reaches a steady state. A cooler is integrated into the circulation and is used to control the temperature in the chemisorption.

EXAMPLE 1

The apparatus consists of an evaporator, a pyrolysis tube in which a bed of magnesium carbonate and calcium carbonate on α-alumina is arranged as a catalyst (diameter of the catalyst from 8 to 14 mm), two condensers and a chemisorption cycle in which a 45% strength aqueous glycolonitrile solution is circulated. The temperature of this solution is brought to +10° C. Chemisorption is carried out in a column, the hydrogen cyanide originating from the pyrolysis and the aqueous glycolonitrile solution being introduced at the top of this column and collected down-stream in a container which is connected to a vacuum pump. In the chemisorption cycle, the solution then passes to the top of the column via a circulating pump and a plurality of metering points.

3.87 kg/hour (86 moles/hour) of formamide are vaporized continuously in the evaporator under 115 mbar, and the vapor is passed through the catalyst heated at 550° C. The pyrolysis gases are cooled to 40° C. in the first condenser and to +10° C. in a second condenser, unconverted formamide and the water formed during the reaction being retained. The cleavage gases then pass into the chemisorption cycle, in which the aqueous glycolonitrile solution is circulated and into which 7,500 g/hour of a 30% strength aqueous formaldehyde solution is fed. The pH in the chemisorption cycle is kept at from 8 to 9. The content of hydrogen cyanide is less than 0.05% at the lower outlet of the column, and falls below the detection limit in the residence tank. Inert gases such as air, carbon monoxide, carbon dioxide and hydrogen, pass through the chemisorption cycle and reach the pressure side of the vacuum pump. 9,500 g/hour of a 45% strength glycolonitrile solution are removed from the chemisorption cycle and are processed to give glycolonitrile after the pressure has been brought to atmospheric pressure.

180 g/hour (6 moles/hour) of reusable formamide are separated off from the two condensers. This gives a yield of glycolonitrile of 93.8%, based on converted formamide, at a conversion of 93% during pyrolysis.

EXAMPLE 2

The apparatus described in Example 1 is used, except that the aqueous glycolonitrile solution in the chemisorption cycle is replaced with a 50% strength solution of lactonitrile in formamide. In contrast to Example 1, brine is passed through the second condenser, so that the pyrolysis gases are cooled therein to a temperature of from −5° to −10° C. 3212 g/hour (73 moles/hour) of acetaldehyde and 5183 g/hour of formamide are fed into the chemisorption cycle at the same time. 10,366 g/hour of a 50% strength solution of lactonitrile in formamide are obtained. This corresponds to a yield of 91.3%, based on a formamide conversion of 93.0% in the pyrolysis reactor.

EXAMPLE 3

The apparatus described in Example 1 is used, and 2115 g/hour (47 moles/hour) of formamide are pyrolyzed therein at 480° C. At a conversion of 88%, 1030 g/hour of hydrogen cyanide pass into the chemisorption cycle, in which 5409 g (90 moles) of ethylenediamine are circulated at 25° C. After one hour, 6430 g of a solution of ethylenediammonium cyanide in excess ethylenediamine are obtained.

We claim:
1. A process for the preparation of a compound which is the reaction product of a carbonyl-containing compound and hydrogen cyanide, which comprises:
   (a) forming HCN by the pyrolysis of formamide or a compound of the formula:

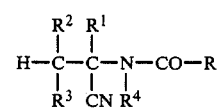

wherein R, $R^1$, $R^2$ and $R^3$ are each H or $C_1$-$C_6$ alkyl, or $R^1$ and $R^2$ or $R^2$ and $R^3$ together form a carbocyclic ring of 5 or 6 carbon atoms, and $R^4$ is H or $C_1$-$C_6$ alkyl, at from 250°-650° C. over a solid catalyst and under a pressure of 5-200 mbar;
   (b) cooling said formed HCN and other products formed by pyrolysis, still under a pressure of 5-200 mbar to a temperature in the range of from 200° to −10° C., thereby separating uncondensed HCN from said other products;
   (c) feeding the cooled uncondensed HCN under a pressure of 5-200 mbar to a chemisorption reaction with a carbonyl-containing compound; and
   (d) removing said reaction product from the reaction mixture.

2. A process as claimed in claim 1, wherein formamide is used for the preparation of the hydrogen cyanide.

3. A process as claimed in claim 1, wherein the carbonyl compound used is an aldehyde of 1 to 4 carbon atoms.

4. A process as claimed in claim 1, wherein the carbonyl compound used is a ketone.

5. A process as claimed in claim 1, wherein an amine of the formula
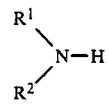
where
R$^1$ and R$^2$ are each C$_1$–C$_8$-alkyl or H, is additionally used.
6. A process as claimed in claim 1, wherein the chemisorption is carried out under from 5 to 140 mbar and at from −20° to +30° C.
* * * * *